United States Patent
Grammenos et al.

(10) Patent No.: US 7,186,861 B2
(45) Date of Patent: Mar. 6, 2007

(54) Z-SUBSTITUTED ACRYLAMIDES, METHODS FOR PRODUCTION THEREOF AND AGENTS COMPRISING THE SAME

(75) Inventors: Wassilios Grammenos, Ludwigshafen (DE); Thomas Grote, Wachenheim (DE); Carsten Blettner, Ludwigshafen (DE); Markus Gewehr, Kastellaun (DE); Andreas Gypser, Mannheim (DE); Bernd Müller, Frankenthal (DE); Joachim Rheinheimer, Ludwigshafen (DE); Peter Schäfer, Ottersheim (DE); Anja Schwögler, Mannheim (DE); Jordi Tormo i Blasco, Laudenbach (DE); Norbert Götz, Worms (DE); Gisela Lorenz, Neustadt (DE); Eberhard Ammermann, Heppenheim (DE); Siegfried Strathmann, Limburgerhof (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 175 days.

(21) Appl. No.: 10/507,605

(22) PCT Filed: Mar. 12, 2003

(86) PCT No.: PCT/EP03/02505

§ 371 (c)(1),
(2), (4) Date: Sep. 14, 2004

(87) PCT Pub. No.: WO03/076392

PCT Pub. Date: Sep. 18, 2003

(65) Prior Publication Data

US 2005/0107619 A1     May 19, 2005

(30) Foreign Application Priority Data

Mar. 14, 2002  (DE) ............................... 102 11 291
Apr. 25, 2002  (DE) ............................... 102 18 619

(51) Int. Cl.
*C07C 233/09*  (2006.01)
*A01N 37/18*  (2006.01)

(52) U.S. Cl. .............. 564/182; 514/183; 514/475; 514/617; 548/967; 549/512; 564/161

(58) Field of Classification Search ............... 564/161, 564/182; 514/475, 617, 183; 548/967; 549/512, 549/551

See application file for complete search history.

(56) References Cited

U.S. PATENT DOCUMENTS 6,130,251 A    10/2000  Seitz et al.
6,696,607 B2    2/2004  Grammenos et al.

FOREIGN PATENT DOCUMENTS

WO    96/17825    6/1996

OTHER PUBLICATIONS

Hirai et al, Heterocycles, vol. 25, pp. 201-204, 1987.*
Patent Abst. of Japan 02200658, 1990.

* cited by examiner

*Primary Examiner*—Shailendra Kumar
(74) *Attorney, Agent, or Firm*—Novak Druce & Quigg, LLP

(57) ABSTRACT

Z-substituted acrylamides of formula (I), where the substituents have the following meanings: X=H, halogen, alkyl, haloalkyl, alkoxy, haloalkoxy, with X in the 3- or 4-position, n=1 or 2, where X can be different if n=2, $R^1$=alkyl, haloalkyl, cycloalkyl, alkoxy, haloalkoxy, aziridine and oxirane and $R^2$=H, alkyl, haloalkyl, allyl, propargyl or $CH_2C\equiv C$-alkyl. Methods for production thereof, agents comprising the above and the use thereof for the treatment of plant-pathogenic fungal pests.

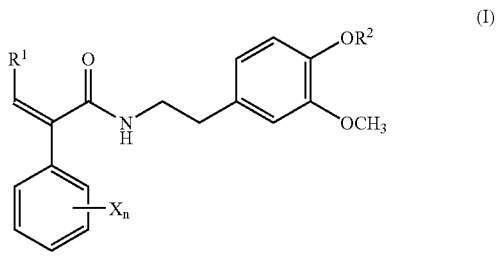

19 Claims, No Drawings

Z-SUBSTITUTED ACRYLAMIDES, METHODS FOR PRODUCTION THEREOF AND AGENTS COMPRISING THE SAME

This application is a 371 of PCT/EP03/02505, filed Mar. 12, 2003.

The present invention relates to Z-substituted acrylamides of the formula I

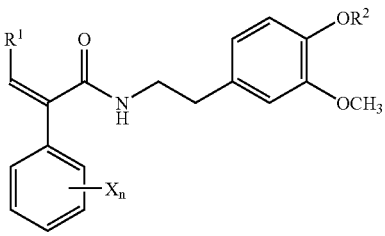

in which the substituents have the following meanings:
X is hydrogen, halogen, $C_1$–$C_4$-alkyl, $C_1$–$C_4$-haloalkyl, $C_1$–$C_4$-alkoxy and $C_1$–$C_4$-haloalkoxy, in which X is in the 3- or 4-position;
n is 1 or 2, it being possible for X to be different if n represents 2;
$R^1$ is $C_1$–$C_4$-alkyl, $C_1$–$C_4$-haloalkyl, $C_3$–$C_5$-cycloalkyl, $C_1$–$C_4$-alkoxy, $C_1$–$C_4$-haloalkoxy, aziridinyl and oxiranyl; and
$R^2$ is hydrogen, $C_1$–$C_4$-alkyl, $C_1$–$C_2$-haloalkyl, allyl, propargyl or $CH_2C\equiv C$—$C_1$–$C_4$-alkyl.

The invention furthermore relates to processes for their preparation, to compositions comprising them and to their use in the control of harmful phytopathogenic fungi.

α-Oximinophenylacetic acid arylamides are described in WO-A 96/17825 and WO-A 96/23763 as fungicides and in JP 02/200 658 as herbicides. Arylacrylamides are included in WO-A 96/17825 only under the general disclosure. WO-A 01/95721 discloses acrylamides with fungicidal action.

Z-Substituted acrylamides are included under the general disclosure of WO-A 01/95721.

The fungicidal action of the compounds described in the abovementioned documents is, however, in many cases unsatisfactory. It is therefore an object of the invention to find compounds with an improved action.

We have found that this object is achieved with Z-substituted acrylamides and compositions comprising them.

The Z-substituted acrylamides are advantageously accessible, starting from carboxylic acids of the formula II and phenethylamines of the formula III, by the route described below:

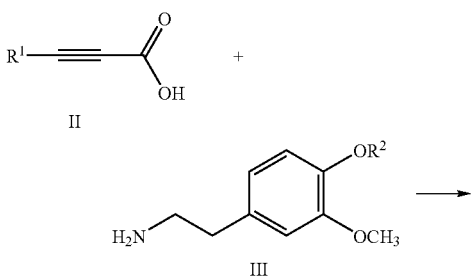

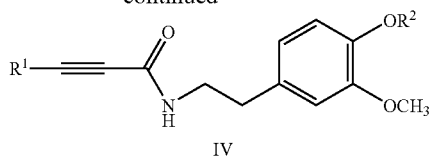

Carboxylic acids of the formula II can be directly amidated in a known way with phenethylamines of the formula III to give compounds of the formula IV [cf. Houben-Weyl, Methoden der Organischen Chemie, Vol. E5, pp. 941–972, Georg Thieme Verlag, Stuttgart and New York, 1985].

The starting materials are generally reacted with one another in equimolar amounts. It may be advantageous to the yield to employ III in an excess with regard to II.

Alternatively, carboxylic acids of the formula II may first be activated before amidation with III, for instance by conversion to acid halides, especially to the acid chlorides.

The starting materials II and III necessary for the preparation of the compounds I are commercially available, are known in the literature [GB-A 2 355 724; Chem. Commun., 1113 (1999); Synthesis (1), 72 (1981); Org. Synth. V, 1043 (1973); CS-B 153 831; DE-A 19 958 165; Bull. Chem. Soc. Jpn., Vol. 63, 1252 (1990)] or can be prepared according to the literature cited.

Phenethylamides of the formula IV are converted into the organotin compounds of the formula V with a trialkyltin hydride in which R is $C_1$–$C_6$-alkyl, for example tributyltin hydride or triphenyltin hydride

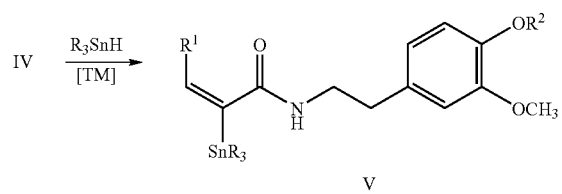

This reaction is usually carried out at temperatures from –20° C. to 80° C., preferably 0° C. to 60° C., in an inert organic solvent in the presence of a catalyst [cf. Tetrahedron, 49 (21), 4677 (1993); ibid., 33(31), 4495 (1992); ibid., 48(40), 8801 (1992); Synth. Commun., 23(2), 143 (1993)].

Suitable solvents are aliphatic hydrocarbons, aromatic hydrocarbons, halogenated hydrocarbons, ethers, such as diethyl ether, diisopropyl ether, tert-butyl methyl ether, dioxane, anisole and tetrahydrofuran, and dimethyl sulfoxide, dimethylformamide and dimethylacetamide, especially preferably tetrahydrofuran and dimethylacetamide. Mixtures of the solvents mentioned can also be used.

The reaction is carried out in the presence of a catalyst, e.g. a transition metal. Suitable transition metal catalysts are iron, cobalt, nickel, rhodium, palladium or platinum compounds, especially nickel(0), nickel(II) and palladium(0) compounds and palladium(II) compounds. Thus, salts, such as nickel chloride, palladium chloride or palladium acetate, or also complexes can be used. The only requirement is that the ligands on the palladium can be displaced from the substrate under the reaction conditions. Phosphine ligands, such as, e.g., arylalkylphosphines, such as, inter alia, methyldiphenylphosphine or isopropyldiphenylphosphine, triarylphosphines, such as, inter alia, triphenylphosphine, tritolylphosphine or trixylylphosphine, trihetarylphosphines, such as trifurylphosphine, or dimeric phosphines, are particularly suitable. Olefinic ligands, such as, inter alia, dibenzylideneacetone or its salts, or cycloocta-1,5-diene, or amines, such as trialkylamines (e.g. triethylamine, tetramethylethylenediamine or N-methylmorpholine) or pyridine are also particularly suitable.

The complex used can be employed directly in the reaction. Thus, the reaction can be carried out, e.g., with bis(triphenylphosphine)nickel(II) bromide, bis(triphenylphosphine)nickel(II) chloride, [1,3-bis(diphenylphosphino)propane]nickel(II) chloride, [1,2-bis(diphenylphosphino)ethane]nickel(II) chloride, tetrakis(triphenylphosphine)palladium(0), bis(triphenylphosphine)palladium dichloride, bis(triphenylphosphine)palladium diacetate, a dibenzylideneacetonepalladium(0) complex, tetrakis(methyldiphenylphosphine)palladium(0) or [1,2-bis(diphenylphosphino)ethane]palladium dichloride. Use may also be made of a nickel or palladium salt and additionally of a suitable ligand which then only in situ form the catalytically active complex. This procedure is available, e.g., for the abovementioned salts and phosphine ligands, such as, e.g., trifurylphosphine or tritolylphosphine. Nickel or palladium complexes, such as, e.g., tris(dibenzylideneacetone)dipalladium, bis(dibenzylideneacetone)palladium or 1,5-cyclooctadienepalladium dichloride, can also be further activated by the addition of ligands, such as, e.g., trifurylphosphine or tritolylphosphine.

Use is generally made of 0.001 to 12 mol %, in particular 0.001 to 5 mol %, of the catalyst, with regard to the starting materials. Higher amounts are possible but are generally unnecessary.

The starting materials are generally reacted with one another in equimolar amounts.

Compounds of the formula V are converted into the compounds of the formula I by transition metal catalysis with phenyl halides of the formula VI in which Hal is bromine or iodine, in particular bromine.

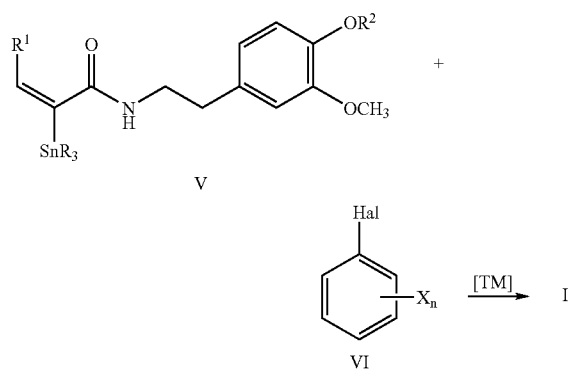

This reaction is generally carried out at temperatures from 0° C. to 80° C., preferably 20° C. to 60° C., in an inert organic solvent in the presence of a transition metal catalyst [TM] [cf. Tetrahedron, 50(41), 12029 (1994); Org. Lett., 2(8), 1121 (2000)].

Suitable solvents are aliphatic hydrocarbons, aromatic hydrocarbons, halogenated hydrocarbons, ethers, such as diethyl ether, diisopropyl ether, tert-butyl methyl ether, dioxane, anisole and tetrahydrofuran, and dimethyl sulfoxide, dimethylformamide and dimethylacetamide, especially preferably tetrahydrofuran, dimethylacetamide and dimethylformamide. Mixtures of the solvents mentioned can also be used.

The reaction is carried out in the presence of a catalyst, e.g. a transition metal. Suitable transition metal catalysts are iron, cobalt, nickel, rhodium, palladium or platinum compounds, especially nickel(0), nickel(II) and palladium(0) compounds and palladium(II) compounds. Thus, salts, such as nickel chloride, palladium chloride or palladium acetate, or also complexes can be used. The only requirement is that the ligands on the palladium can be displaced from the substrate under the reaction conditions. Phosphine ligands, such as, e.g., arylalkylphosphines, such as, inter alia, methyldiphenylphosphine or isopropyldiphenylphosphine, triarylphosphines, such as, inter alia, triphenylphosphine, tritolylphosphine or trixylylphosphine, trihetarylphosphines, such as trifurylphosphine, or dimeric phosphines, are particularly suitable. Olefinic ligands, such as, inter alia, dibenzylideneacetone or its salts, or cycloocta-1,5-diene, or amines, such as trialkylamines (e.g. triethylamine, tetramethylethylenediamine or N-methylmorpholine) or pyridine are also particularly suitable.

The complex used can be employed directly in the reaction. Thus, the reaction can be carried out, e.g., with bis(triphenylphosphine)nickel(II) bromide, bis(triphenylphosphine)nickel(II) chloride, [1,3-bis(diphenylphosphino)propane]nickel(II) chloride, [1,2-bis(diphenylphosphino)ethane]nickel(II) chloride, tetrakis(triphenylphosphine)palladium(0), bis(triphenylphosphine)palladium dichloride, bis(triphenylphosphine)palladium diacetate, a dibenzylideneacetonepalladium(0) complex, tetrakis(methyldiphenylphosphine)palladium(0) or [1,2-bis(diphenylphosphino)ethane]palladium dichloride. Use may also be made of a nickel or palladium salt and additionally of a suitable ligand which then only in situ form the catalytically active complex. This procedure is available, e.g., for the abovementioned salts and phosphine ligands, such as, e.g., trifurylphosphine or tritolylphosphine. Nickel or palladium complexes, such as, e.g., tris(dibenzylideneacetone)dipalladium, bis(dibenzylideneacetone)palladium or 1,5-cyclooctadienepalladium dichloride, can also be further activated by the addition of ligands, such as, e.g., trifurylphosphine or tritolylphosphine.

The reaction is advantageously carried out in the presence of copper(I) salts, such as, e.g., Cu(I)I, as additional catalyst.

Use is generally made of 0.001 to 12 mol %, in particular 0.001 to 5 mol %, of the catalyst, with regard to the starting materials. Higher amounts are possible but are generally unnecessary.

The starting materials are generally reacted with one another in equimolar amounts. It may be advantageous to the yield to employ VI in an excess with regard to V.

The reaction mixtures are worked up in the usual way, e.g. by mixing with water, separation of the phases and, if appropriate, chromatographic purification of the crude products. In some cases, the intermediates and final products are obtained in the form of colorless or slightly brownish, viscous oils, which are freed or purified from volatile components under reduced pressure and at moderately elevated temperature. If the intermediates and final products are obtained as solids, the purification can also be carried out by recrystallization or trituration.

If individual compounds I are not accessible by the routes described above, they can be prepared by derivatization of other compounds I.

Collective terms were used in the definitions of the symbols given in the above formulae, which collective terms are generally representative of the following substituents:

halogen: fluorine, chlorine, bromine and iodine;

alkyl: saturated, straight-chain or branched hydrocarbon radicals with 1 to 4 carbon atoms, e.g. methyl, ethyl, propyl, 1-methylethyl, butyl, 1-methylpropyl, 2-methylpropyl and 1,1-dimethylethyl;

haloalkyl: straight-chain or branched alkyl groups with 1 to 4 carbon atoms (as mentioned above), it being possible for the hydrogen atoms in these groups to be partially or completely replaced by halogen atoms as mentioned above, e.g. $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups with 1 to 8 carbon atoms (as mentioned above) which are bonded to the backbone via an oxygen atom (—O—);

haloalkoxy: straight-chain or branched haloalkyl groups with 1 to 4 carbon atoms (as mentioned above) which are bonded to the backbone via an oxygen atom (—O—).

In view of the intended use of the acrylamides of the formula I, the following meanings of the substituents, in each case alone or in combination, are particularly preferred:

The particularly preferred embodiments of the intermediates with regard to the variables correspond to those of the radicals $X_n$, $R^1$ and $R^2$ of the formula I.

Preferred compounds I are those in which $R^1$ represents $C_1$–$C_4$-alkyl, halomethyl or $C_3$–$C_5$-cycloalkyl.

Particularly preferred compounds I are those in which $R^1$ represents methyl, ethyl, isopropyl, tert-butyl, trifluoromethyl, cyclopropyl or cyclopentyl.

Particularly preferred compounds I are in addition those in which $R^2$ is methyl, ethyl, propargyl, $C_2$-haloalkyl, in particular 2,2,2-trifluoroethyl, or allyl.

Particularly preferred compounds I are those in which X is not hydrogen.

Moreover, particularly preferred compounds I are those in which n represents 1 and X is in the 4-position.

Likewise, particularly preferred compounds I are those in which n represents 2 and X is in the 3,4-position.

In addition, particularly preferred compounds I are those in which $R^2$ is hydrogen. They are valuable not only as active compounds but also as intermediates in the preparation of additional compounds I.

The compounds I compiled in the following tables are particularly preferred in view of their use. The groups mentioned in the tables for a substituent furthermore represent, considered per se, independently of the combination in which they are mentioned, a particularly preferred embodiment of the substituent in question.

Table 1

Compounds of the formula I in which $R^1$ and $R^2$ are methyl and the radical $X_n$ corresponds to one row of table A for each compound.

Table 2

Compounds of the formula I in which $R^1$ is methyl and $R^2$ is ethyl and the radical $X_n$ corresponds to one row of table A for each compound.

Table 3

Compounds of the formula I in which $R^1$ is methyl and $R^2$ is propargyl and the radical $X_n$ corresponds to one row of table A for each compound.

Table 4

Compounds of the formula I in which $R^1$ is methyl and $R^2$ is 2,2,2-trifluoroethyl and the radical $X_n$ corresponds to one row of table A for each compound.

Table 5

Compounds of the formula I in which $R^1$ is methyl and $R^2$ is allyl and the radical $X_n$ corresponds to one row of table A for each compound.

Table 6

Compounds of the formula I in which $R^1$ is ethyl and $R^2$ is methyl and the radical $X_n$ corresponds to one row of table A for each compound.

Table 7

Compounds of the formula I in which $R^1$ and $R^2$ are ethyl and the radical $X_n$ corresponds to one row of table A for each compound.

Table 8

Compounds of the formula I in which $R^1$ is ethyl and $R^2$ is propargyl and the radical $X_n$ corresponds to one row of table A for each compound.

Table 9

Compounds of the formula I in which $R^1$ is ethyl and $R^2$ is 2,2,2-trifluoroethyl and the radical $X_n$ corresponds to one row of table A for each compound.

Table 10

Compounds of the formula I in which $R^1$ is ethyl and $R^2$ is allyl and the radical $X_n$ corresponds to one row of table A for each compound.

Table 11

Compounds of the formula I in which $R^1$ is isopropyl and $R^2$ is methyl and the radical $X_n$ corresponds to one row of table A for each compound.

Table 12

Compounds of the formula I in which $R^1$ is isopropyl and $R^2$ is ethyl and the radical $X_n$ corresponds to one row of table A for each compound.

Table 13

Compounds of the formula I in which $R^1$ is isopropyl and $R^2$ is propargyl and the radical $X_n$ corresponds to one row of table A for each compound.

Table 14

Compounds of the formula I in which $R^1$ is isopropyl and $R^2$ is 2,2,2-trifluoroethyl and the radical $X_n$ corresponds to one row of table A for each compound.

Table 15

Compounds of the formula I in which $R^1$ is isopropyl and $R^2$ is allyl and the radical $X_n$ corresponds to one row of table A for each compound.

Table 16

Compounds of the formula I in which $R^1$ is tert-butyl and $R^2$ is methyl and the radical $X_n$ corresponds to one row of table A for each compound.

Table 17

Compounds of the formula I in which $R^1$ is tert-butyl and $R^2$ is ethyl and the radical $X_n$ corresponds to one row of table A for each compound.

Table 18
Compounds of the formula I in which $R^1$ is tert-butyl and $R^2$ is propargyl and the radical $X_n$ corresponds to one row of table A for each compound.

Table 19
Compounds of the formula I in which $R^1$ is tert-butyl and $R^2$ is 2,2,2-trifluoroethyl and the radical $X_n$ corresponds to one row of table A for each compound.

Table 20
Compounds of the formula I in which $R^1$ is tert-butyl and $R^2$ is allyl and the radical $X_n$ corresponds to one row of table A for each compound.

Table 21
Compounds of the formula I in which $R^1$ is trifluoromethyl and $R^2$ is methyl and the radical $X_n$ corresponds to one row of table A for each compound.

Table 22
Compounds of the formula I in which $R^1$ is trifluoromethyl and $R^2$ is ethyl and the radical $X_n$ corresponds to one row of table A for each compound.

Table 23
Compounds of the formula I in which $R^1$ is trifluoromethyl and $R^2$ is propargyl and the radical $X_n$ corresponds to one row of table A for each compound.

Table 24
Compounds of the formula I in which $R^1$ is trifluoromethyl and $R^2$ is 2,2,2-trifluoroethyl and the radical $X_n$ corresponds to one row of table A for each compound.

Table 25
Compounds of the formula I in which $R^1$ is trifluoromethyl and $R^2$ is allyl and the radical $X_n$ corresponds to one row of table A for each compound.

Table 26
Compounds of the formula I in which $R^1$ is cyclopropyl and $R^2$ is methyl and the radical $X_n$ corresponds to one row of table A for each compound.

Table 27
Compounds of the formula I in which $R^1$ is cyclopropyl and $R^2$ is ethyl and the radical $X_n$ corresponds to one row of table A for each compound.

Table 28
Compounds of the formula I in which $R^1$ is cyclopropyl and $R^2$ is propargyl and the radical $X_n$ corresponds to one row of table A for each compound.

Table 29
Compounds of the formula I in which $R^1$ is cyclopropyl and $R^2$ is 2,2,2-trifluoromethyl and the radical $X_n$ corresponds to one row of table A for each compound.

Table 30
Compounds of the formula I in which $R^1$ is cyclopropyl and $R^2$ is allyl and the radical $X_n$ corresponds to one row of table A for each compound.

Table 31
Compounds of the formula I in which $R^1$ is cyclobutyl and $R^2$ is methyl and the radical $X_n$ corresponds to one row of table A for each compound.

Table 32
Compounds of the formula I in which $R^1$ is cyclobutyl and $R^2$ is ethyl and the radical $X_n$ corresponds to one row of table A for each compound.

Table 33
Compounds of the formula I in which $R^1$ is cyclobutyl and $R^2$ is propargyl and the radical $X_n$ corresponds to one row of table A for each compound.

Table 34
Compounds of the formula I in which $R^1$ is cyclobutyl and $R^2$ is 2,2,2-trifluoromethyl and the radical $X_n$ corresponds to one row of table A for each compound.

Table 35
Compounds of the formula I in which $R^1$ is cyclobutyl and $R^2$ is allyl and the radical $X_n$ corresponds to one row of table A for each compound.

Table 36
Compounds of the formula I in which $R^1$ is cyclopentyl and $R^2$ is methyl and the radical $X_n$ corresponds to one row of table A for each compound.

Table 37
Compounds of the formula I in which $R^1$ is cyclopentyl and $R^2$ is ethyl and the radical $X_n$ corresponds to one row of table A for each compound.

Table 38
Compounds of the formula I in which $R^1$ is cyclopentyl and $R^2$ is propargyl and the radical $X_n$ corresponds to one row of table A for each compound.

Table 39
Compounds of the formula I in which $R^1$ is cyclopentyl and $R^2$ is 2,2,2-trifluoromethyl and the radical $X_n$ corresponds to one row of table A for each compound.

Table 40
Compounds of the formula I in which $R^1$ is cyclopentyl and $R^2$ is allyl and the radical $X_n$ corresponds to one row of table A for each compound.

TABLE A

| No. | $X_n$ |
|---|---|
| A-1 | 3-Cl |
| A-2 | 4-Cl |
| A-3 | 3-F |
| A-4 | 4-F |
| A-5 | 3-Br |
| A-6 | 4-Br |
| A-7 | 3-I |
| A-8 | 4-I |
| A-9 | 3-$CH_3$ |
| A-10 | 4-$CH_3$ |
| A-11 | 3-$CH_2CH_3$ |
| A-12 | 4-$CH_2CH_3$ |
| A-13 | 3-$CH_2CH_2CH_3$ |
| A-14 | 4-$CH_2CH_2CH_3$ |
| A-15 | 3-$CH(CH_3)_2$ |
| A-16 | 4-$CH(CH_3)_2$ |
| A-17 | 3-$C(CH_3)_3$ |
| A-18 | 4-$C(CH_3)_3$ |
| A-19 | 3-$CF_3$ |
| A-20 | 4-$CF_3$ |
| A-21 | 3-$OCH_3$ |
| A-22 | 4-$OCH_3$ |
| A-23 | 3-$OCH_2CH_3$ |
| A-24 | 4-$OCH_2CH_3$ |
| A-25 | 3-$OCH_2CH_2CH_3$ |
| A-26 | 4-$OCH_2CH_2CH_3$ |
| A-27 | 3-$OCH(CH_3)_2$ |
| A-28 | 4-$OCH(CH_3)_2$ |
| A-29 | 3-$OCF_3$ |
| A-30 | 4-$OCF_3$ |
| A-31 | 3-$OCHF_2$ |
| A-32 | 4-$OCHF_2$ |

TABLE A-continued

| No. | $X_n$ |
|---|---|
| A-33 | 3,4-$F_2$ |
| A-34 | 3,4-$Cl_2$ |
| A-35 | 3-F-4-Br |
| A-36 | 3-Cl-4-Br |
| A-37 | 3-Cl-4-$CH_3$ |
| A-38 | 3-Cl-4-$OCH_3$ |
| A-39 | 3-Cl-4-$OCF_3$ |
| A-40 | 3-Cl-4-$OCHF_2$ |
| A-41 | 3,4-$(CH_3)_2$ |
| A-42 | 3,4-$(CH_2CH_3)_2$ |
| A-43 | 3-$CH_3$-4-$CH_2CH_3$ |
| A-44 | 3-$CH_2CH_3$-4-$CH_3$ |
| A-45 | 3,4-$(OCH_3)_2$ |
| A-46 | 3,4-$(OCH_2CH_3)_2$ |
| A-47 | 3-$OCH_3$-4-$OCH_2CH_3$ |
| A-48 | 3-$OCH_2CH_3$-4-$OCH_3$ |
| A-49 | 3-$OCH_3$-4-$OCH_2CH_2CH_3$ |
| A-50 | 3-$OCH_2CH_2CH_3$-4-$OCH_3$ |
| A-51 | 3-$OCH_2CH_3$-4-$OCH_2CH_2CH_3$ |
| A-52 | 3-$OCH_2CH_2CH_3$-4-$OCH_2CH_3$ |
| A-53 | 3-$OCH_3$-4-$OCH(CH_3)_2$ |
| A-54 | 3-$OCH(CH_3)_2$-4-$OCH_3$ |
| A-55 | 3-$OCH_3$-4-$OCF_3$ |
| A-56 | 3-$OCF_3$-4-$OCH_3$ |
| A-57 | 3-$CH_3$-4-$OCF_3$ |
| A-58 | 3-$CH_3$-4-$OCHF_2$ |
| A-59 | 3-$CH_3$-4-Cl |
| A-60 | 3-$CH_3$-4-$OCH_3$ |
| A-61 | 3-$OCH_3$-4-Cl |
| A-62 | 3-$OCH_3$-4-$CH_3$ |
| A-63 | 3-$CH_3$-4-$OCF_3$ |
| A-64 | 3-$CH_3$-4-Br |
| A-65 | 3-$CH_3$-4-Br |
| A-66 | 3-$OCH_3$-4-Br |

The compounds I are suitable as fungicides. They are distinguished through an outstanding effectiveness against a broad spectrum of phytopathogenic fungi, especially from the classes of the Ascomycetes, Deuteromycetes, Phycomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:
  *Alternaria* species on fruit and vegetables,
  *Botrytis cinerea* (gray mold) on strawberries, vegetables, ornamental plants and grapevines,
  *Cercospora arachidicola* on peanuts,
  *Erysiphe cichoracearum* and *Sphaerotheca fuliginea* on cucurbits,
  *Blumeria graminis* (powdery mildew) on cereals,
  *Fusarium* and *Verticillium* species on various plants,
  *Helminthosporium* species on cereals,
  *Mycosphaerella* species on bananas and peanuts,
  *Phytophthora infestans* on potatoes and tomatoes,
  *Plasmopara viticola* on grapevines,
  *Podosphaera leucotricha* on apples,
  *Pseudocercosporella herpotrichoides* on wheat and barley,
  *Pseudoperonospora* species on hops and cucumbers,
  *Puccinia* species on cereals,
  *Pyricularia oryzae* on rice,
  *Rhizoctonia* species on cotton, rice and lawns,
  *Septoria nodorum* on wheat,
  *Uncinula necator* on grapevines,
  *Ustilago* species on cereals and sugar cane, and
  *Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the effect desired. Amounts customarily applied in the protection of materials are, for example, 0.001 g to 2 kg, preferably 0.005 g to 1 kg, of active compound per cubic meter of treated material.

The compounds I can be converted into the usual formulations, e.g. solutions, emulsions, suspensions, dusts, powders, pastes and granules. The application form depends on the respective use intended; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalensulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol, polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel fuel, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, combinations for broadcasting and dusts can be prepared by mixing or mutually grinding the active substances with a solid carrier.

Granules, e.g. coated granules, impregnated granules and homogeneous granules, can be prepared by binding the active compounds to solid carriers. Solid carriers are, e.g., mineral earths, such as silicic acids, silica gels, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

EXAMPLES FOR FORMULATIONS ARE

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecylbenzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are intimately mixed with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100 000 parts by weight of water and finely dispersing it therein, an aqueous dispersion is obtained comprising 0.02% by weight of the active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20 000 parts by weight of water.

The active compounds can be used as such, in the form of their formulations or the application forms prepared therefrom, e.g. in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; they should in any case guarantee the finest possible dispersion of the active compounds according to the invention.

Aqueous use forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, concentrates comprising active substance, wetting agent, tackifier, dispersant or emulsifier and possibly solvent or oil can also be prepared, which concentrates are suitable for dilution with water.

The concentrations of active compound in the ready-for-use compositions can be varied within relatively wide ranges. In general, they are between 0.0001 and 10%, preferably between 0.01 and 1%.

The active compounds can also be used with great success in the ultra low volume (ULV) process, it being possible to apply formulations with more than 95% by weight of active compound or even the active compound without additives.

Oils of various types, herbicides, fungicides, other pesticides and bactericides can be added to the active compounds, if need be too not until immediately before use (tank mix). These agents can be added to the compositions according to the invention in a weight ratio of 1:10 to 10:1.

The compositions according to the invention can, in the application form as fungicides, also be present together with other active compounds, e.g. with herbicides, insecticides, growth regulators, fungicides or also with fertilizers. On mixing the compounds I or the compositions comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N'-ethylenebisdithiocarbamate), ammonia complex of zinc (N,N'-propylenebisdithiocarbamate), zinc (N,N'-propylenebisdithiocarbamate) or N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate or diisopropyl 5-nitroisophthalate;

heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-(methoxycarbonylamino)benzimidazole, 2-(2-furyl) benzimidazole, 2-(4-thiazolyl)benzimidazole, N-(1,1,2,2-tetrachloroethylthio)tetrahydrophthalimide, N-(trichloromethylthio)tetrahydrophthalimide or N-(trichloromethylthio)phthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazin-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-(tert-butyl)phenyl)-2-methylpropyl]-cis-2,6-dimethylmorpholine, N-[3-(p-(tert-butyl)phenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-(n-propyl)-1,3-dioxolan-2-ylmethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene or 1,2-bis(3-methoxycarbonyl-2-thioureido)benzene, strobilurins, such as methyl E-methoxyimino[α-(o-tolyloxy)-o-tolyl]acetate, methyl E-2-{2-[6-(2-cyanophenoxy)pyrimidin-4-yloxy]phenyl}-3-methoxyacrylate, methyl E-methoxyimino(2-phenoxyphenyl)acetamide, methylE-methoxyimino[α-(2,5-dimethylphenoxy)-o-tolyl]acetamide, methyl E-2-{2-[[2-trifluoromethylpyrid-6-yl]oxymethyl]phenyl}-3-methoxyacrylate, methyl (E,E)-methoxyimino{2-[1-(3-trifluoromethylphenyl)ethylideneaminooxymethyl]phenyl}acetate or methyl N-(2-{[1-(4-chlorophenyl)-1H-pyrazol-3-yl]oxymethyl}phenyl)-N-methoxycarbamate, anilinopyrimidines, such as N-(4,6-dimethylpyrimidin-2-yl)aniline, N-[4-methyl-6-(1-propynyl)pyrimidin-2-yl]aniline or N-[4-methyl-6-cyclopropylpyrimidin-2-yl]aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloylmorpholine or 3-(4-fluorophenyl-3-(3,4-dimethoxyphenyl)acryloylmorpholine, and various fungicides, such as dodecylguanidine acetate, 1-(3-bromo-6-methoxy-2-methylphenyl)-[(2,3,4-trimethoxy-6-methylphenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, N-(2,6-dimethylphenyl)-N-(2'-methoxyacetyl)-DL-alanine methyl ester, N-(2,6-dimethylphenyl)-N-chloroacetyl-D,L-2-aminobutyrolactone, N-(2,6-dimethylphenyl)-N-(phenylacetyl)-DL-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-N-(ethylaminocarbonyl)-2-[methoxyimino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis(4-fluorophenyl)methylsilyl)methyl)-1H-1,2,4-triazole, 5-chloro-2-cyano-4-(p-tolyl)imidazole-1-sulfonic acid dimethylamide or 3,5-dichloro-N-(3-chloro-1-ethyl-1-methyl-2-oxopropyl)-4-methylbenzamide.

Synthesis Examples

The procedures described in the following synthesis examples were used to prepare further compounds I by appropriate modification of the starting materials. The compounds thus obtained are listed in the following table, together with physical data.

Example 1

Synthesis of 5-isopropyl-2,4-dihydro-3H-pyrazol-3-one 70 g (1.26 mol) of hydrazine hydrate were added dropwise at 10 to 30° C. to a solution of 100 g (0.62 mol) of ethyl isobutyrylacetate in 60 ml of ethanol. After the exothermic reaction had subsided, the mixture was stirred at 20 to 25°

C. for a further 14 hours approximately and was then cooled to approximately −10° C. 52 g of the title compound were isolated by filtration.

$^1$H NMR [δ (CDCl$_3$)]: 9.5 (br, 1H); 5.25 (s, 1H); 2.75 (q, 1H); 1.1 (d, 6H).

Example 2

Synthesis of 4,4-dibromo-5-isopropyl-2,4-dihydro-3H-pyrazol-3-one 140 g (0.87 mol) of bromine were added dropwise to 52 g (0.41 mol) of the pyrazolone from example 1 in 300 ml of glacial acetic acid and the mixture was stirred at 20 to 25° C. for approximately 14 hours. The mixture was subsequently poured into ice-water and the precipitate was filtered off. 113 g of the title compound were obtained.

$^1$H NMR [δ (CDCl$_3$)]: 9.5 (br, 1H); 3.0 (q, 1H); 1,35 (d, 6H).

Example 3

Synthesis of 4-methyl-2-pentynoic Acid 60 g (0.21 mol) of the pyrazolone from example 2 in 150 ml of methyl tert-butyl ether (MTBE) were added dropwise at 0° C. to 400 ml of 10% aqueous sodium hydroxide solution and the combined mixture was stirred at 20 to 0.25° C. for 3 hours. The aqueous phase was separated, brought with concentrated hydrochloric acid to pH 2.5 and extracted with MTBE, and the organic extract was dried. After removal of the solvent, 23.3 g of the title compound were obtained.

$^1$H NMR [δ (CDCl$_3$)]: 8.0 (br, OH); 2.7 (q, 1H); 1.2 (d, 6H).

Example 4

Synthesis of N-[2-(3,4-dimethoxyphenyl)ethyl]-4-methyl-2-pentynamide

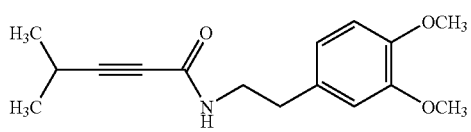

38.2 g (280 mmol) of isobutyl chloroformate were added dropwise at 0 to 5° C., as well as 28.3 g (280 mmol) of N-methylmorpholine at 5 to 15° C., to a solution of 28.4 g (254 mmol) of 4-methyl-2-pentynoic acid (ex. 3) in 100 ml of tetrahydrofuran (THF). 46 g (254 mmol) of homoveratrylamine were subsequently added dropwise while cooling with ice and the mixture was allowed to stir at 20 to 25° C. for 48 hours. The reaction solution was then concentrated and the residue was poured into water/10% hydrochloric acid solution and extracted with MTBE. After drying, distilling off the volatile components and chromatographing on silica gel (cyclohexane:MTBE [3:1]), 44 g of the title compound were obtained.

$^1$H NMR [δ (CDCl$_3$)]: 6.85–6.6 (m, 3H); 5.75 (m, 1H); 3.85 (s, 3H); 3.80 (s, 3H); 3.5 (q, 2H).

Example 5

Synthesis of (2E)-N-[2-(3,4-dimethoxyphenyl)ethyl]-4-methyl-2-(tributylstannyl)-2-pentenamide

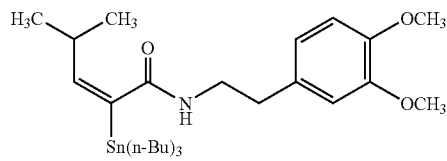

0.8 g of Pd(PPh$_3$)$_4$ was added to the solution of 47.1 g (170 mmol) of the amide from ex. 4 in 200 ml of THF and then 51 g (175 mmol) of tributyltin hydride in 50 ml of THF were added dropwise at 15 to 20° C. After stirring for approximately 14 hours at 20 to 25° C., the reaction solution was concentrated and the residue was poured into dilute hydrochloric acid and extracted with MTBE. After drying, distilling off the volatile components and chromatographing on silica gel (cyclohexane:MTBE [3:1]), 88.8 g of the title compound were obtained as a viscous oil.

$^1$H NMR [δ (CDCl$_3$)]: 6.8–6.7 (m, 3H); 5.4 (d, 1H); 5.2 (m, 1H); 3.9 (s, 3H); 3.85 (s, 3H).

Example 6

Synthesis of (2Z)-2-(4-chlorophenyl)-N-[2-(3,4-dimethoxyphenyl)ethyl]-4-methyl-2-pentenamide
[I-2]

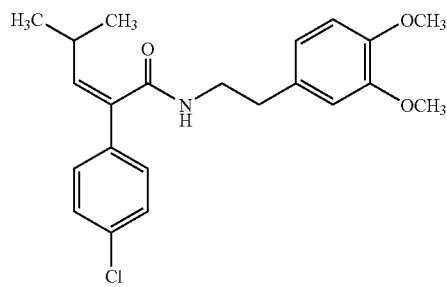

A solution of 10 g (17.6 mmol) of (2E)-N-[2-(3,4-dimethoxyphenyl)ethyl]-4-methyl-2-(tributylstannyl)-2-pentenamide (5) in 15 ml of dimethylformamide (DMF) was mixed with 4.2 g (17.7 mmol) of 4-chloroiodobenzene, 0.5 g of Pd(PPh$_3$)$_4$ and 0.5 g of copper(I) iodide. After stirring for approximately 14 hours at 20 to 25° C., the reaction solution was poured into water and extracted with MTBE. The organic phases were washed with water, dried and freed from the solvent. After chromatographing on silica gel (cyclohexane:MTBE [7:1 to 1:1]), 5.8 g of the title compound were obtained.

$^1$H NMR [δ (CDCl$_3$)]: 1.0 (d, 6H); 2.8 (m, 1H); 2.9 (t, 2H); 3.8 (q, 2H); 3.92 (s, 3H); 3.97 (s, 3H); 5.6 (m, NH); 5.9 (d, 1H); 6.7–6.9 (m, 3H) and 7.2–7.3 (m, 4H).

TABLE I

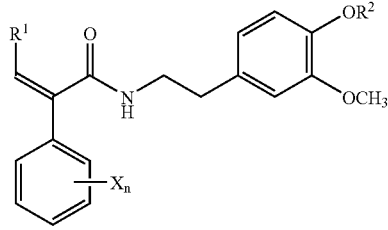

| Nr. | $X_n$ | $R^1$ | $R^2$ | Phys. data (M.p. [°C]; $^1$H-HMR δ [ppm]; M [m/ee]) |
|---|---|---|---|---|
| I-1 | 4-Cl | $CH_2CH_3$ | $CH_2CH_3$ | 2.25(p); 2.8(t); 3.6(q) |
| I-2 | 4-Cl | $CH(CH_3)_2$ | $CH_3$ | (see ex. 6) |
| I-3 | 4-Cl | $C(CH_3)_3$ | $CH_2CH_3$ | oil |
| I-4 | 4-$CF_3$ | $CH_2CH_3$ | $CH_3$ | 110–111 |
| I-5 | 3,4-$Cl_2$ | $CH_2CH_3$ | $CH_3$ | 93–96 |
| I-6 | 4-Br | $CH_2CH_3$ | $CH_3$ | 112–114 |
| I-7 | 4-$C(CH_3)_3$ | $CH_2CH_3$ | $CH_3$ | 2.8(t); 3.6(q); 3.8(s) |
| I-8 | H | $CH_2CH_3$ | $CH_3$ | 58–60 |
| I-9 | 3,4-$(CH_3)_2$ | $CH_2CH_3$ | $CH_3$ | 77–79 |
| I-10 | 3-$CH_3$-4-$OCH_3$ | $CH_2CH_3$ | $CH_3$ | 64 |
| I-11 | 3-$OCH_3$ | $CH_2CH_3$ | $CH_3$ | 2.8(t); 3.6(q); 5.6(t) |
| I-12 | 4-F | $CH_2CH_3$ | $CH_3$ | 132–134 |
| I-13 | 3-Cl-4-$CH_3$ | $CH_2CH_3$ | $CH_3$ | 57–60 |
| I-14 | 4-$OCF_3$ | $CH_2CH_3$ | $CH_3$ | 103–105 |
| I-15 | 3-F-4-Br | $CH_2CH_3$ | $CH_3$ | 87–89 |
| I-16 | 4-$CH_2CH_3$ | $CH_2CH_3$ | $CH_3$ | 92–93 |
| I-17 | 4-$OCH_2CH_3$ | $CH_2CH_3$ | $CH_3$ | 96–97 |
| I-18 | 3-Cl-4-F | $CH_2CH_3$ | $CH_3$ | 85–86 |
| I-19 | 4-Cl | $CH_2CH_3$ | $CH_3$ | 98–100 |
| I-20 | 4-$OCH_3$ | $CH_2CH_3$ | $CH_3$ | 2.3(q); 2.8(q); 3.6(q) |
| I-21 | 4-Cl | $CH(CH_3)_2$ | $CH_2CH_3$ | 2.65(h); 2.8(t); 3.75(s) |
| I-22 | 3,4-$Cl_2$ | $CH(CH_3)_2$ | $CH_2CH_3$ | oil |
| I-23 | 3,4-$Cl_2$ | $CH_3$ | $CH_3$ | 2.8(t); 2.6(q); 3.8(s) |
| I-24 | 3-$OCH_3$ | $CH_3$ | $CH_3$ | 3.6(q); 3.8(s); 3.85(s) |
| I-25 | 4-$CF_3$ | $CH_3$ | $CH_3$ | 2.8(t); 3.7(q); 3.8(s) |
| I-26 | 4-Br | $CH_3$ | $CH_3$ | 1.9(d); 2.8(t); 3.6(q) |
| I-27 | 4-$C(CH_3)_3$ | $CH_3$ | $CH_3$ | 1.85(d); 2.8(t); 3.6(q) |
| I-28 | 3,4-$(CH_3)_2$ | $CH_3$ | $CH_3$ | 1.9(d); 2.8(t); 3.6(q) |
| I-29 | 4-Cl | $CH_3$ | $CH_3$ | 2.8(s); 3.6(d); 3.8(s) |
| I-30 | 4-$OCH_3$ | $CH_3$ | $CH_3$ | 1.9(d); 2.8(t); 3.6(q) |
| I-31 | 4-$OCH_3$ | $CH_2CH_3$ | $CH_2CH_3$ | oil |
| I-32 | 4-$C(CH_3)_3$ | $CH_2CH_3$ | $CH_2CH_3$ | 1.35(s); 1.45(t); 2.8(t) |
| I-33 | 4-Br | $CH_2CH_3$ | $CH_2CH_3$ | 98–101 |
| I-34 | 3,4-$(CH_3)_2$ | $CH_2CH_3$ | $CH_2CH_3$ | 1.05(t); 1.4(t); 2.8(t) |
| I-35 | 3-$CH_3$-4-$OCH_3$ | $CH_2CH_3$ | $CH_2CH_3$ | 80–81 |
| I-36 | 3-$OCH_3$ | $CH_2CH_3$ | $CH_2CH_3$ | 93–94 |
| I-37 | 3-Cl-4-$CH_3$ | $CH_2CH_3$ | $CH_2CH_3$ | 76–78 |
| I-38 | 3-Cl-4-F | $CH_2CH_3$ | $CH_2CH_3$ | 75 |
| I-39 | 4-$OCF_3$ | $CH_2CH_3$ | $CH_2CH_3$ | 82–84 |
| I-40 | 3-F-4-Br | $CH_2CH_3$ | $CH_2CH_3$ | 85–87 |
| I-41 | 4-$CH_2CH_3$ | $CH_2CH_3$ | $CH_2CH_3$ | 77–79 |
| I-42 | 4-$OCH_3$ | $CH_2CH_3$ | $CH_2CH_3$ | 88–90 |
| I-43 | 4-$CF_3$ | $CH_2CH_3$ | $CH_2CH_3$ | 103–104 |
| I-44 | 3,4-$Cl_2$ | $CH_2CH_3$ | $CH_2CH_3$ | 65 |
| I-45 | H | $CH_2CH_3$ | $CH_2CH_3$ | 86–88 |
| I-46 | 4-F | $CH_2CH_3$ | $CH_2CH_3$ | 87–89 |
| I-47 | 4-$CH(CH_3)_2$ | $CH_2CH_3$ | $CH_3$ | 1.05(t); 2.8(t); 3.8(s) |
| I-48 | 4-$CH(CH_3)_2$ | $CH_2CH_3$ | $CH_3$ | 85–87 |
| I-49 | 4-$OCH_3$ | $CH(CH_3)_2$ | $CH_3$ | 3.6(q); 3.8(s); 7.13(s) |
| I-50 | 4-$CF_3$ | $CH(CH_3)_2$ | $CH_3$ | 2.65(h); 2.8(t); 3.6(q) |
| I-51 | 4-$C(CH_3)_3$ | $CH(CH_3)_2$ | $CH_3$ | 3.6(t); 3.8(s); 3.85(s) |
| I-52 | 4-Br | $CH(CH_3)_2$ | $CH_3$ | 2.8(t); 3.6(q); 3.85(s) |
| I-53 | 4-$CH(CH_3)_2$ | $CH(CH_3)_2$ | $CH_3$ | 2.8(t); 3.6(q); 3.8(s) |
| I-54 | 4-$OCF_3$ | $CH(CH_3)_2$ | $CH_3$ | 2.8(t); 3.6(q); 3.8(s) |
| I-55 | 3-$CH_3$-4-$OCH_3$ | $CH(CH_3)_2$ | $CH_3$ | 1.0(s); 1.05(s); 2.8(t) |
| I-56 | 3-F-4-Br | $CH(CH_3)_2$ | $CH_3$ | 2.65(h); 2.8(t); 3.8(s) |
| I-57 | 4-$C(CH_3)_3$ | $C(CH_3)_3$ | $CH_2CH_3$ | 2.8(t); 3.6(q); 3.8(s) |
| I-58 | 3,4-$Cl_2$ | $C(CH_3)_3$ | $CH_2CH_3$ | 1.15(s); 2.8(t); 3.6(q) |
| I-59 | 4-F | $C(CH_3)_3$ | $CH_2CH_3$ | oil |
| I-60 | 3,4-$(CH_3)_2$ | $C(CH_3)_3$ | $CH_2CH_3$ | 76–79 |
| I-61 | 3-$CH_3$-4-$OCH_3$ | $C(CH_3)_3$ | $CH_2CH_3$ | 70–73 |
| I-62 | H | $C(CH_3)_3$ | $CH_2CH_3$ | 75–78 |
| I-63 | 3-$OCH_3$ | $C(CH_3)_3$ | $CH_2CH_3$ | 103–106 |

TABLE I-continued

| Nr. | $X_n$ | $R^1$ | $R^2$ | Phys. data (M.p. [°C.]; $^1$H-HMR δ [ppm]; M [m/ee]) |
|---|---|---|---|---|
| I-64 | 3-F-4-Cl | C(CH$_3$)$_3$ | CH$_2$CH$_3$ | 2.8(t); 3.75(s); 4.05(q) |
| I-65 | 3-F-4-Br | C(CH$_3$)$_3$ | CH$_2$CH$_3$ | 1.4(t); 2.8(t); 4.05(q) |
| I-66 | 4-OCH$_2$CH$_3$ | C(CH$_3$)$_3$ | CH$_2$CH$_3$ | 1.15(s); 2.8(t); 3.75(s) |
| I-67 | 4-CH$_2$CH$_3$ | C(CH$_3$)$_3$ | CH$_2$CH$_3$ | 2.8(t); 3.6(q); 3.8(s) |
| I-68 | 4-CH(CH$_3$)$_2$ | C(CH$_3$)$_3$ | CH$_2$CH$_3$ | 2.8(t); 2.9(h); 3.6(q) |
| I-69 | 4-Br | C(CH$_3$)$_3$ | CH$_2$CH$_3$ | 2.8(t); 3.6(q); 3.8(s) |
| I-70 | 3-Cl-4-CH$_3$ | C(CH$_3$)$_3$ | CH$_2$CH$_3$ | 2.8(t); 3.6(q); 3.75(s) |
| I-71 | 4-OCF$_3$ | C(CH$_3$)$_3$ | CH$_2$CH$_3$ | 3.6(q); 3.8(s); 4.1(q) |
| I-72 | 4-OCH$_3$ | C(CH$_3$)$_3$ | CH$_2$CH$_3$ | 2.8(t); 3.6(q); 4.1(q) |
| I-73 | 4-CF$_3$ | C(CH$_3$)$_3$ | CH$_2$CH$_3$ | 2.8(t); 3.6(q); 3.8(s) |
| I-74 | 3,4-(CH$_3$)$_2$ | C(CH$_3$)$_3$ | CH$_2$CH$_3$ | 2.8(t); 3.6(q); 3.8(s) |
| I-75 | 3-CH$_3$-4-OCH$_3$ | C(CH$_3$)$_3$ | CH$_3$ | 2.8(t); 3.6(q); 3.75(s) |
| I-76 | H | C(CH$_3$)$_3$ | CH$_3$ | 2.8(t); 3.6(q); 3.75(s) |
| I-77 | 4-F | C(CH$_3$)$_3$ | CH$_3$ | 2.8(t); 3.6(q); 3.8(s) |
| I-78 | 3-Cl-4-F | C(CH$_3$)$_3$ | CH$_3$ | 2.8(t); 3.6(q); 5.5(t) |
| I-79 | 3-CH$_3$-4-Cl | C(CH$_3$)$_3$ | CH$_3$ | 2.35(s); 2.8(t); 3.6(q) |
| I-80 | 4-OCF$_3$ | C(CH$_3$)$_3$ | CH$_3$ | 2.8(t); 3.6(q); 5.5(t) |
| I-81 | 3-F-4-Br | C(CH$_3$)$_3$ | CH$_3$ | 2.8(t); 3.6(q); 3.8(s) |
| I-82 | 4-CH$_2$CH$_3$ | C(CH$_3$)$_3$ | CH$_3$ | 2.6(q); 2.75(t); 3.55(q) |
| I-83 | 4-OCH$_2$CH$_3$ | C(CH$_3$)$_3$ | CH$_3$ | 2.8(t); 3.6(q); 3.8(s) |
| I-84 | 4-CH(CH$_3$)$_2$ | C(CH$_3$)$_3$ | CH$_3$ | 2.8(t); 3.6(q); 3.8(s) |
| I-85 | 4-Cl | C(CH$_3$)$_3$ | CH$_3$ | 2.8(t); 3.6(q); 3.8(s) |
| I-86 | 3,4-Cl$_2$ | C(CH$_3$)$_3$ | CH$_3$ | 2.8(t); 3.6(q); 3.8(s) |
| I-87 | 4-OCH$_3$ | C(CH$_3$)$_3$ | CH$_3$ | 2.8(t); 3.6(q); 3.85(s) |
| I-88 | 3-OCH$_3$ | C(CH$_3$)$_3$ | CH$_3$ | 2.8(t); 3.6(q); 3.85(s) |
| I-89 | 4-C(CH$_3$)$_3$ | C(CH$_3$)$_3$ | CH$_3$ | 1.2(s); 2.8(t); 3.6(q) |
| I-90 | 4-CF$_3$ | C(CH$_3$)$_3$ | CH$_3$ | 1.15(s); 2.75(t); 3.6(q); |
| I-91 | 4-Br | C(CH$_3$)$_3$ | CH$_3$ | 2.75(t); 3.6(q); 3.75(s) |
| I-92 | H | CH(CH$_3$)$_2$ | CH$_2$CH$_3$ | 3.6(q); 3.75(s); 4.05(q) |
| I-93 | 4-OCH$_3$ | CH(CH$_3$)$_2$ | CH$_2$CH$_3$ | 3.6(q); 3.8(s); 4.0(Q) |
| I-94 | 4-CF$_3$ | CH(CH$_3$)$_2$ | CH$_2$CH$_3$ | 3.6(q); 3.75(s); 4.0(q) |
| I-95 | 4-C(CH$_3$)$_3$ | CH(CH$_3$)$_2$ | CH$_2$CH$_3$ | 3.6(q); 3.75(s); 4:05(q) |
| I-96 | 4-Br | CH(CH$_3$)$_2$ | CH$_2$CH$_3$ | 2.8(t); 3.6(q); 3.8(s) |
| I-97 | 4-F | CH(CH$_3$)$_2$ | CH$_2$CH$_3$ | 2.8(t); 3.65(q); 3.8(s) |
| I-98 | 4-CH(CH$_3$)$_2$ | CH(CH$_3$)$_2$ | CH$_2$CH$_3$ | 3.65(q); 3.8(s); 4:05(q) |
| I-99 | 4-CH$_2$CH$_3$ | CH(CH$_3$)$_2$ | CH$_2$CH$_3$ | 3.6(q); 3.8(s); 4.05(q) |
| I-100 | 4-OCH$_2$CH$_3$ | CH(CH$_3$)$_2$ | CH$_2$CH$_3$ | 2.8(t); 3.6(q); 3.8(s) |
| I-101 | 3-CH$_3$-4-OCH$_3$ | CH(CH$_3$)$_2$ | CH$_2$CH$_3$ | 2.8(t); 3.6(q); 3.8(s) |
| I-102 | 3-OCH$_3$ | CH(CH$_3$)$_2$ | CH$_2$CH$_3$ | 2.8(t); 3.6(q); 3.8(s) |
| I-103 | 3,4-(CH$_3$)$_2$ | CH(CH$_3$)$_2$ | CH$_2$CH$_3$ | 3.6(q); 3.8(s); 5.7(d) |
| I-104 | 3,4-Cl$_2$ | CH$_3$ | CH$_2$CH$_3$ | 2.8(t); 3.65(q); 3.8(s) |
| I-105 | 4-OCH$_3$ | CH$_3$ | CH$_2$CH$_3$ | 2.8(t); 3.6(q); 3.8(s) |
| I-106 | 4-Br | CH$_3$ | CH$_2$CH$_3$ | 2.8(t); 3.6(q); 3.8(s) |
| I-107 | 3,4-(CH$_3$)$_2$ | CH$_3$ | CH$_2$CH$_3$ | 2.8(t); 3.6(q); 3.8(s) |
| I-108 | 4-CH(CH$_3$)$_2$ | CH$_3$ | CH$_2$CH$_3$ | 2.8(t); 2.85(h); 4.0(q) |
| I-109 | 4-Cl | CH$_3$ | CH$_2$CH$_3$ | 2.8(t); 3.6(q); 3.8(s) |
| I-110 | 4-CF$_3$ | CH$_3$ | CH$_2$CH$_3$ | 2.8(t); 3.65(q); 3.8(s) |
| I-111 | 3-CH$_3$-4-Cl | CH(CH$_3$)$_2$ | CHF$_2$ | oil |
| I-112 | 4-Cl | CH(CH$_3$)$_2$ | CHF$_2$ | 100–102 |
| I-113 | 4-F | CH(CH$_3$)$_2$ | CHF$_2$ | 70–72.5 |
| I-114 | 3,4-(CH$_3$)$_2$ | CH(CH$_3$)$_2$ | CHF$_2$ | 75–79 |
| I-115 | 3,4-Cl$_2$ | CH(CH$_3$)$_2$ | CHF$_2$ | 63–66 |
| I-116 | 4-CF$_3$ | CH(CH$_3$)$_2$ | CHF$_2$ | 47–49 |
| I-117 | 4-OCH$_3$ | CH(CH$_3$)$_2$ | CHF$_2$ | 62–65 |
| I-118 | 4-OCF$_3$ | CH(CH$_3$)$_2$ | CHF$_2$ | 2.85(t); 3.65(q); 3.8(s) |
| I-119 | 4-Br | CH(CH$_3$)$_2$ | CHF$_2$ | 103–105 |
| I-120 | 4-CH$_2$CH$_3$ | CH(CH$_3$)$_2$ | CHF$_2$ | 55–57 |
| I-121 | 4-OCH$_2$CH$_3$ | CH(CH$_3$)$_2$ | CHF$_2$ | 95–97 |
| I-122 | 4-C(CH$_3$)$_3$ | CH(CH$_3$)$_2$ | CHF$_2$ | 54–59 |
| I-123 | 3-OCH$_3$ | CH(CH$_3$)$_2$ | CHF$_2$ | 53–60 |
| I-124 | 3-Cl-4-CH$_3$ | CH(CH$_3$)$_2$ | CHF$_2$ | 67–72 |
| I-125 | 3-Cl-4-F | CH(CH$_3$)$_2$ | CHF$_2$ | 3.65(q); 3.75(s); 5.75(d) |
| I-126 | 4-CH(CH$_3$)$_2$ | CH(CH$_3$)$_2$ | CHF$_2$ | 76–77 |

TABLE I-continued

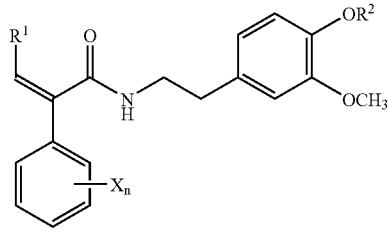

| Nr. | Xn | R[1] | R[2] | Phys. data (M.p. [°C.]; $^1$H-HMR δ [ppm]; M [m/ee]) |
|---|---|---|---|---|
| I-127 | 3-CH$_3$-4-OCH$_3$ | CH(CH$_3$)$_2$ | CHF$_2$ | 102 |
| I-128 | 4-Cl | C(CH$_3$)$_3$ | CHF$_2$ | 48–51 |
| I-129 | 4-F | C(CH$_3$)$_3$ | CHF$_2$ | 54–56 |
| I-130 | 3,4-(CH$_3$)$_2$ | C(CH$_3$)$_3$ | CHF$_2$ | 2.8(t); 3.6(q); 3.75(s) |
| I-131 | 3,4-Cl$_2$ | C(CH$_3$)$_3$ | CHF$_2$ | 2.8(t); 3.65(q); 3.75(s) |
| I-132 | 4-Br | C(CH$_3$)$_3$ | CHF$_2$ | 66–67 |
| I-133 | 4-CF$_3$ | C(CH$_3$)$_3$ | CHF$_2$ | 64–66.5 |
| I-134 | 4-OCH$_3$ | C(CH$_3$)$_3$ | CHF$_2$ | 2.75(t); 3.5(q); 3.75(s) |
| I-135 | 4-OCF$_3$ | C(CH$_3$)$_3$ | CHF$_2$ | 2.8(t); 3.5(q); 3.75(s) |
| I-136 | 4-CH$_2$CH$_3$ | C(CH$_3$)$_3$ | CHF$_2$ | 7.13(d); 7.4(m); 7.75(d) |
| I-137 | 4-Cl | c-C$_6$H$_{11}$ | CH$_3$ | 3.85(s); 3.8(s); 5.8(d) |
| I-138 | 4-Cl | c-C$_6$H$_{11}$ | CH$_2$CH$_3$ | 4.05(q); 3.8(s); 3.6(q) |
| I-139 | H | c-C$_3$H$_5$ | CH$_3$ | 5.3(d); 3.6(q); 2.8(q) |
| I-140 | 4-F | c-C$_3$H$_5$ | CH$_2$CH$_3$ | 2.85(q); 3.8(q); 5.75(NH) |
| I-141 | 4-CF$_3$ | c-C$_3$H$_5$ | CH$_3$ | 3.6(q); 3.8(s); 3.9(s); 5.3(d) |
| I-142 | 4-Br | c-C$_3$H$_5$ | CH$_3$ | 2.75(q); 3.75(q); 5.3(d) |
| I-143 | 4-OCH$_3$ | c-C$_3$H$_5$ | CH$_3$ | 5.25(d); 3.9(s); 3.85(s) |
| I-144 | 4-CH$_2$CH$_3$ | c-C$_3$H$_5$ | CH$_3$ | 5.2(d); 3.5(q); 2.8(q) |
| I-145 | 4-CH(CH$_3$)$_2$ | c-C$_3$H$_5$ | CH$_3$ | 1.2(d); 2.0(m) |
| I-146 | 4-C(CH$_3$)$_3$ | c-C$_3$H$_5$ | CH$_3$ | 1.3(s); 5.3(d) |
| I-147 | 3,4-Cl$_2$ | c-C$_3$H$_5$ | CH$_3$ | 5.3(d); 0.5(m); 0.8(d) |
| I-148 | 3,4-CH$_3$ | c-C$_3$H$_5$ | CH$_3$ | 5.2(d); 2.2(s); 2.75(s) |
| I-149 | 3-CH$_3$-4-OCH$_3$ | c-C$_3$H$_5$ | CH$_3$ | 5.2(d); 2.8(d); 3.8(d) |
| I-150 | 4-Cl | c-C$_3$H$_5$ | CH$_2$CH$_3$ | 4.0(q); 3.8(s); 3.6(q) |
| I-151 | 3,4-Cl$_2$ | c-C$_3$H$_5$ | CH$_2$CH$_3$ | 4.0(q); 3.8(s); 2.8(q) |
| I-152 | 4-CH$_3$ | c-C$_3$H$_5$ | CH$_2$CH$_3$ | 5.2(d); 4.0(q); 3.8(s) |
| I-153 | 3,4-(CH$_3$)$_2$ | c-C$_3$H$_5$ | CH$_2$CH$_3$ | 4.1(q); 3.8(s); 3.6(q) |
| I-154 | 4-Br | c-C$_3$H$_5$ | CH$_2$CH$_3$ | 113–115 |
| I-155 | 4-CF$_3$ | c-C$_3$H$_5$ | CH$_2$CH$_3$ | 120–121 |
| I-156 | 4-OCF$_3$ | c-C$_3$H$_5$ | CH$_2$CH$_3$ | 100 |
| I-157 | 3-Cl-4-CH$_3$ | c-C$_3$H$_5$ | CH$_2$CH$_3$ | 5.2(d); 4.0(q); 3.8(s) |
| I-158 | 4-OCH$_3$ | c-C$_3$H$_5$ | CH$_2$CH$_3$ | 82–85 |
| I-159 | 4-OCH$_2$CH$_3$ | CH(CH$_3$)$_2$ | CH$_3$ | m/e 398 (M + 1) |
| I-160 | 4-F—3-CH$_3$ | CH(CH$_3$)$_2$ | CH$_3$ | m/e 386 (M + 1) |
| I-161 | CH$_2$CH$_3$ | CH(CH$_3$)$_2$ | CH$_3$ | m/e 382 (M + 1) |
| I-162 | 4-CH$_3$ | CH(CH$_3$)$_2$ | CH$_3$ | m/e 368 (M + 1) |
| I-163 | 4-Br | CH(CH$_2$CH$_3$)$_2$ | CH$_3$ | 2.8(t); 3.65(t); 3.8(s); 3.85(s) |
| I-164 | 4-CF$_3$ | CH(CH$_2$CH$_3$)$_2$ | CH$_3$ | 1.3(m); 1.5(m); 2.85(t); 3.65(t) |
| I-165 | 4-Cl | CH(CH$_2$CH$_3$)$_2$ | CH$_3$ | 1.3(m); 1.5(m); 2.35(m); 5.5(s); 5.6(d) |
| I-166 | 4-CH$_3$ | CH(CH$_2$CH$_3$)$_2$ | CH$_3$ | 2.35(d); 2.8(m); 3.6(m); 3.8(s); 5.5(m); |
| I-167 | 4-CH$_2$CH$_3$ | CH(CH$_2$CH$_3$)$_2$ | CH$_3$ | 0.9(m); 2.4(m); 2.6(m); 5.5(s) |
| I-168 | 4-OCH$_3$ | CH(CH$_2$CH$_3$)$_2$ | CH$_3$ | 2.35(m); 2.8(m); 3.6(m); 5.5(s); 5.6(d) |
| I-169 | 4-CH$_3$—3-Cl | CH(CH$_2$CH$_3$)$_2$ | CH$_3$ | 2.3(s); 3.0(m); 3.6(m); 5.5(s); 5.6(d) |
| I-170 | 4-CH(CH$_2$)$_2$ | CH(CH$_2$CH$_3$)$_2$ | CH$_3$ | 1.25(d); 2.35(m); 2.8(m); 2.9(m); 5.6(d) |
| I-171 | 4-F—3-Cl | CH(CH$_2$CH$_3$)$_2$ | CH$_3$ | 1.25(m); 1.5(m); 2.3(m); 2.8(m); 5.5(s); 5.75(d) |
| I-172 | 3,4-Cl$_2$ | CH(CH$_2$CH$_3$)$_2$ | CH$_3$ | 1.3(m); 1.5(m); 2.3(m); 2.8 m); 5.5(s); 5.75(d) |
| I-173 | 4-C(CH$_3$)$_3$ | CH(CH$_2$CH$_3$)$_2$ | CH$_3$ | 83–85 |
| I-174 | 4-Br—3-F | CH(CH$_2$CH$_3$)$_2$ | CH$_3$ | 1.3(m); 1.5(m); 2.25(m); 2.8(m); 3.6(m) |
| I-175 | 4-OCH$_3$-3-CH$_3$ | CH(CH$_2$CH$_3$)$_2$ | CH$_3$ | 1.3(m); 1.5(m); 2.2(m); 2.4(m); 2.8(t) |
| I-176 | 3,4-(CH$_3$)$_2$ | CH(CH$_2$CH$_3$)$_2$ | CH$_3$ | 69–72 |
| I-177 | 4-OCH$_2$CH$_3$ | CH(CH$_2$CH$_3$)$_2$ | CH$_3$ | 2.35(m); 2.8(m); 3.6(m); 4.0(t) |
| I-178 | 4-OCF$_3$ | CH(CH$_2$CH$_3$)$_2$ | CH$_3$ | 1.3(m); 1.5(m); 2.3(m); 2.8(t); 3.65(m) |
| I-179 | 3-OCH$_3$ | CH(OH$_2$CH$_3$)$_2$ | CH$_3$ | 63–65 |
| I-180 | 4-Cl | C(CH$_3$)$_2$OCH$_3$ | CH$_3$ | 83–86 |
| I-181 | 4-CF$_3$ | C(CH$_3$)$_2$OCH$_3$ | CH$_3$ | 1.4(s); 2.8(m); 3.2(s); 3.6(m); 3.8(s); 3.85(s); 5.95(s) |
| I-182 | 4-CH$_3$ | C(CH$_3$)$_2$OCH$_3$ | CH$_3$ | 1.4(m); 2.8(m); 3.2(s); 3.65(m) |
| I-183 | 4-C(CH$_3$)$_3$ | C(CH$_3$)$_2$OCH$_3$ | CH$_3$ | 1.3(s); 1.4(m); 2.8(m); 3.2(s) |
| I-184 | 4-CH$_3$—3-Cl | C(CH$_3$)$_2$OCH$_3$ | CH$_3$ | 112–115 |
| I-185 | 4-Br | C(CH$_3$)$_2$OCH$_3$ | CH$_3$ | 1.4(s); 2.8(m); 3.2(s); 3.6(m) |
| I-186 | 4-F | C(CH$_3$)$_2$OCH$_3$ | CH$_3$ | 1.5(s); 2.8(t); 3.2(s); 3.65(m) |
| I-187 | 4-OCH$_3$—3-CH$_3$ | C(CH$_3$)$_2$OCH$_3$ | CH$_3$ | 1.5(m); 2.25(m); 2.8(t); 3.2(s) |

TABLE I-continued

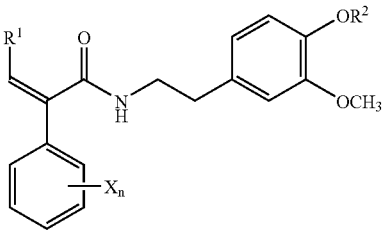

| Nr. | $X_n$ | $R^1$ | $R^2$ | Phys. data (M.p. [°C.]; $^1$H-HMR δ [ppm]; M [m/ee]) |
|---|---|---|---|---|
| I-188 | 4-OCF$_3$ | C(CH$_3$)$_2$OCH$_3$ | CH$_3$ | 1.4(s); 2.8(t); 3.2(s); 3.65(m) |
| I-189 | 4-Br | CH(CH$_3$)CH$_2$CH$_3$ | CH$_3$ | 0.9(s); 1.0(s); 2.5(t); 2.8(t) |
| I-190 | 4-C(CH$_3$)$_3$ | CH(CH$_3$)CH$_2$CH$_3$ | CH$_3$ | 0.9(t); 1.0(d); 1.25(s); 3.65(m) |
| I-191 | 4-F | CH(CH$_3$)CH$_2$CH$_3$ | CH$_3$ | 2.5(m); 2.9(m); 3.65(m); 5.7(d) |
| I-192 | 4-OCF$_3$ | CH(CH$_3$)CH$_2$CH$_3$ | CH$_3$ | 2.5(m); 2.8(t); 3.7(m); 3.9(d) |
| I-193 | 4-OCH$_3$—3-CH$_3$ | CH(CH$_3$)CH$_2$CH$_3$ | CH$_3$ | 0.9(t); 1.0(d); 2:25(s); 2.8(t) |
| I-194 | 4-CF$_3$ | CH(CH$_3$)CH$_2$CH$_3$ | CH$_3$ | 0.9(t); 1.0(d); 1.55(s); 2.5(m); 2.8(t) |
| I-195 | 4-Cl | CH(CH$_3$)CH$_2$CH$_3$ | CH$_3$ | 0.9(t); 1.0(d); 1.4(m); 2.25(s); 2.8(t) |
| I-196 | 4-CH$_3$ | CH(CH$_3$)CH$_2$CH$_3$ | CH$_3$ | 0.9(t); 1.0(d); 1.4(m); 2.5(m); 3.7(m) |
| I-197 | 4-Cl | c-C$_3$H$_5$ | CH$_3$ | 117—120 |
| I-198 | 4-CH$_3$ | c-C$_3$H$_5$ | CH$_3$ | 102–105 |
| I-199 | 4-Br—3-F | c-C$_3$H$_5$ | CH$_3$ | 115–118 |
| I-200 | 4-CH$_3$-3-Cl | c-C$_3$H$_5$ | CH$_3$ | 0.5(t); 0.9(m); 2.0(m); 2.8(t) |
| I-201 | 4-Br—3-CH$_3$ | c-C$_3$H$_5$ | CH$_3$ | 0.5(t); 0.9(m); 2.0(m); 2.75(m) |
| I-202 | 4-CH$_3$ | C(CH$_3$)$_3$ | CH$_3$ | 1.15(s); 2.4(t); 2.8(t); 3.65(m) |
| I-203 | 4-Br—3-CH$_3$ | C(CH$_3$)$_3$ | CH$_3$ | 1.15(s); 2.4(t); 2.8(t); 3.8(s) |
| I-204 | 4-Br | c-C$_5$H$_9$ | CH$_2$CH$_3$ | 74–79 |
| I-205 | 4-Br—3-CH$_3$ | c-C$_5$H$_9$ | CH$_2$CH$_3$ | 82–86 |
| I-206 | 4-Br | c-C$_5$H$_9$ | CH$_3$ | 108–113 |
| I-207 | 4-Br—3-CH$_3$ | c-C$_5$H$_9$ | CH$_3$ | 81–84 |
| I-208 | 4-Br | C(CH$_3$)$_2$OCH$_3$ | CH$_2$CH$_3$ | 1.4(s); 1.5(t); 2.8(t); 3.25(s) |
| I-209 | 4-CF$_3$ | C(CH$_3$)$_2$OCH$_3$ | CH$_2$CH$_3$ | 1.4(s); 1.45(t); 2.75(m); 3.25(s); 3.8(s) |
| I-210 | 4-CH$_3$ | C(CH$_3$)$_2$OCH$_3$ | CH$_2$CH$_3$ | 2.8(m); 3.25(s); 3.6(m); 3.75(s) |
| I-211 | 4-Cl | C(CH$_3$)$_2$OCH$_3$ | CH$_2$CH$_3$ | 1.35(s); 1.45(t); 2.8(m); 3.2(s) |
| I-212 | 4-CH$_3$—3-Br | C(CH$_3$)$_2$OCH$_3$ | CH$_2$CH$_3$ | 1.35(s); 1.45(t); 2.8(t); 4.1(m) |
| I-213 | 3,4-Cl$_2$ | C(CH$_3$)$_2$OCH$_3$ | CH$_2$CH$_3$ | 1.35(s); 1.45(t); 3.2(s); 4.1(s); 5.9(s) |
| I-214 | 3,4-(CH$_3$)$_2$ | C(CH$_3$)$_2$OCH$_3$ | CH$_2$CH$_3$ | 1.35(s); 1.45(t); 3.2(s); 4.1(s); 5.9(s) |
| I-215 | 3-OCH$_3$ | C(CH$_3$)$_2$OCH$_3$ | CH$_2$CH$_3$ | 2.8(m); 3.2(s); 3.65(m); 3.85(s) |
| I-216 | 4-F—3-Cl | C(CH$_3$)$_2$OCH$_3$ | CH$_2$CH$_3$ | 1.3(s); 1.5(t); 2.75(m); 3.2(s); 3.8(s) |
| I-217 | 4-Br—3-F | C(CH$_3$)$_2$OCH$_3$ | CH$_2$CH$_3$ | 1.4(s); 2.8(t); 3.2(s); 3.6(m) |
| I-218 | 4-CH$_2$CH$_3$ | C(CH$_3$)$_2$OCH$_3$ | CH$_2$CH$_3$ | 2.6(s); 2.75(m); 3.25(s) 3.75(s); 4.1(m) |
| I-219 | 4-F | C(CH$_3$)$_2$OCH$_3$ | CH$_2$CH$_3$ | 1.45(s); 1.5(t); 2.8(t); 3.2(s); 3.6(m) |
| I-220 | C(CH$_3$)$_3$ | C(CH$_3$)$_2$OCH$_3$ | CH$_2$CH$_3$ | 2.8(t); 3.2(s); 3.65(m); 3.8(s) |
| I-221 | 4-OCH$_3$—3-CH$_3$ | C(CH$_3$)$_2$OCH$_3$ | CH$_2$CH$_3$ | 2.8(m); 3.25(s); 3.6(m); 3.80(s); 3.85(s) |
| I-222 | 4-OCF$_3$ | C(CH$_3$)$_2$OCH$_3$ | CH$_2$CH$_3$ | 1.4(s); 2.8(m); 3.25(s); 3.6(m); 3.80(s); 4.1(m) |
| I-223 | 4-Br | CH(CH$_3$)CH$_2$CH$_3$ | CH$_2$CH$_3$ | 2.5(m); 2.8(m); 3.6(m); 4.1(m) |
| I-224 | 4-Cl | CH(CH$_3$)CH$_2$CH$_3$ | CH$_2$CH$_3$ | 2.5(m); 2.8(t); 3.6(m); 3.65(m); 3.8(s) |
| I-225 | 4-CF$_3$ | CH(CH$_3$)CH$_2$CH$_3$ | CH$_2$CH$_3$ | 2.8(m); 3.25(s); 3.6(m); 3.80(s); 3.85(s) |
| I-226 | 4-F | CH(CH$_3$)CH$_2$CH$_3$ | CH$_2$CH$_3$ | 2.5(m); 2.8(t); 3.6(m); 3.75(s); 4.1(m) |
| I-227 | 4-OCH$_3$—3-CH$_3$ | CH(CH$_3$)CH$_2$CH$_3$ | CH$_2$CH$_3$ | 2.5(m); 2.8(t); 3.6(m); 3.75(s); 4.1(m) |
| I-228 | 4-CH$_3$—3-Br | CH(CH$_3$)CH$_2$CH$_3$ | CH$_2$CH$_3$ | 0.9(t); 1.0(d); 2.5(m); 2.8(t); 3.6(t) |
| I-229 | 3,4-Cl$_2$ | CH(CH$_3$)CH$_2$CH$_3$ | CH$_2$CH$_3$ | 0.9(t); 1.0(d); 2.5(m); 3.8(s); 5.75(d) |
| I-230 | 4-CH$_3$ | CH(CH$_3$)CH$_2$CH$_3$ | CH$_2$CH$_3$ | 0.9(t); 1.0(d); 2.5(m); 2.8(t); 3.6(m) |
| I-231 | 4-Br—3-Cl | c-C$_3$H$_5$ | CH$_3$ | 105–111 |
| I-232 | 4-Br—3-Cl | CH$_2$CH$_3$ | CH$_3$ | 95–113 |
| I-233 | 4-Br—3-Cl | CH$_2$CH$_3$ | CH$_3$ | 103–105 |
| I-234 | 4-Br—3-CH$_3$ | CH$_2$CH$_3$ | CH$_2$CH$_3$ | 92–94 |
| I-235 | 4-Cl—3-CH$_3$ | CH$_2$CH$_3$ | CH$_3$ | 94–99 |
| I-236 | 4-Cl—3-CH$_3$ | CH$_2$CH$_3$ | CH$_2$CH$_3$ | 70–80 |
| I-237 | 4-Cl—3-CH$_3$ | CH(CH$_3$)$_2$ | CH$_3$ | 116–118 |
| I-238 | 4-Cl—3-CH$_3$ | CH(CH$_3$)$_2$ | CH$_2$CH$_3$ | 94–95 |
| I-239 | 4-Cl—3-CH$_3$ | C(CH$_3$)$_3$ | CH$_2$CH$_3$ | 0.95(t); 2.3(d); 2.8(t) 3.6(m); 3.75(s) |
| I-240 | 4-Cl—3-CH$_3$ | c-C$_3$H$_5$ | CH$_3$ | 117–120 |
| I-241 | 4-F—3-Cl | c-C$_3$H$_5$ | CH$_3$ | 93–98 |
| I-242 | 4-Br—3-CH$_3$ | C(CH$_3$)$_3$ | CH$_2$CH$_3$ | 1.15(s); 1.35(t); 2.25(s); 2.8(m); 3.65(m); 3.75(s); 4.0(m); 5.8(s) |
| I-243 | 4-Br | C(CH$_3$)$_3$ | CH$_2$—C≡CC$_2$H$_5$ | 1.0(t); 1.1(s); 2.25(q); 2.75(q); 3.5(q); 3.7(s); 4.6(s); 5.6(s); 5.8(s); 6.6(m); 6.85(m); 7.2(m); 7.4(m) | c-C$_3$H$_5$ = cyclopropyl
c-C$_5$H$_9$ = cyclopentyl

Examples for the Action Against Harmful Fungi

The fungicidal action of the compounds of the formula I can be demonstrated from the following tests:

The active compounds were prepared, separately or together, as a 10% emulsion in a mixture of 70% by weight of cyclohexanone, 20% by weight of Nekanil® LN (Lutensol® AP6, wetting agent with an emulsifying and dispersing action based on ethoxylated alkylphenols) and 10% by weight of Wettol® EM (nonionic emulsifier based on ethoxylated castor oil) and were appropriately diluted with water to the desired concentration.

The compound A, known as compound No. I-17 from WO-A 01/95721, was used as comparative active compound:

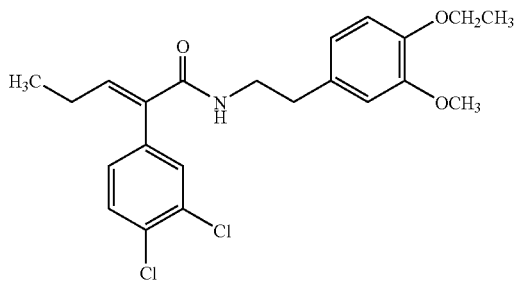

Comparative Example

Activity Against Downy Mildew of Grapes Caused by *Plasmopara viticola* (Lasting Effect)

Leaves of potted vines of the variety "Müller-Thurgau" were sprayed to runoff point with an aqueous preparation of active compound prepared from a stock solution consisting of 10% of active compound, 85% of cyclohexanone and 5% of emulsifier. In order to be able to assess the lasting effects of the substances, the plants, after the spray coating had dried on, were placed in a greenhouse for 7 days. Only then were the leaves inoculated with an aqueous suspension of zoospores of *Plasmopara viticola*. The vines were then initially placed in a chamber saturated with water vapor at 24° C. for 48 hours and subsequently in a greenhouse at temperatures of between 20 and 30° C. for 5 days. After this period of time, the plants were once more placed in a humid chamber for 16 hours to accelerate the eruption of sporangiphores. The extent to which the infection had developed on the undersides of the leaves was then determined visually.

In this test, the plants treated with 63 ppm of the active compound I-44 showed 3% infection, while the plants treated with 63 ppm of the comparative active compound A were 40% infected and the untreated plants were 90% infected.

Use Example 1

Activity Against Downy Mildew of Grapes Caused by *Plasmopara viticola*

The plants treated with 250 ppm of the active compounds I-1 to I-23, I-26 to I-50, I-52 to I-87, I-89 to I-101, I-103 to I-112, I-128, I-130, I-132, I-134 and I-136 showed, under the experimental conditions described above, no or up to 15% infection, while the untreated plants were 90% infected.

Use Example 2

Activity Against Tomato Blight Caused by *Phytophthora infestans*

The use of pot plants of the variety "Große Fleischtomate St. Pierre" were sprayed to runoff point with an aqueous suspension prepared from a stock solution consisting of 10% of active compound, 85% of cyclohexanone and 5% of emulsifier. On the following day, the leaves were infected with a cold aqueous suspension of zoospores of *Phytophthora infestans* with a concentration of $0.25 \times 10^6$ spores/ml. The plants were subsequently placed in a chamber saturated with water vapor at temperatures between 18 and 20° C. After 6 days, the tomato blight in the untreated but infected control plants had so extensively developed that the infection could be visually determined in %.

In this test, the plants treated with 250 ppm of the active compounds I-1 to I-7, I-9 to I-11, I-13 to I-23, I-26, I-28, I-29, I-31, I-33 to I-35, I-37 to I-44, I-46 to I-52, I-54, I-55, I-57 to I-88, I-90, I-91, I-93 to I-97, I-99, I-101, I-103 to I-111, I-128, I-130, I-139 to I-158, I-180 to I-182, I-184, I-185, I-187, I-188, I-197 to I-203, I-208 to I-218, I-221, I-223, I-224 and I-228 to I-240 showed no or up to 15% infection, while the untreated plants were 100% infected.

Use Example 3

Activity Against Downy Mildew of Grapes Caused by *Plasmopara viticola*

The use of potted vines of the variety "Müller-Thurgau" were sprayed to runoff point with an aqueous suspension of active compound at the concentration given below. The suspension or emulsion was prepared from a stock solution with 10% of active compound in a mixture consisting of 85% of cyclohexanone, and 5% of emulsifier. On the following day, the undersides of the leaves were inoculated with an aqueous suspension of zoospores of *Plasmopara viticola*. The vines were then initially placed in a chamber saturated with water vapor at 24° C. for 48 hours and subsequently in a greenhouse at temperatures of between 20 und 30° C. for 5 days. After this period of time, the plants were once more placed in a humid chamber for 16 hours to accelerate the eruption of the sporangiphores. The extent to which the infection had developed on the undersides of the leaves was then determined visually.

In this test, the plants treated with 250 ppm of the active compounds I-150 to I-158, I-168, I-171, I-180 to I-189, I-194 to I-204, I-207 to I-225 and I-227 to I-240 showed no or up to 7% infection, while the untreated plants were 90% infected.

We claim:
1. A Z-substituted acrylamide of the formula I

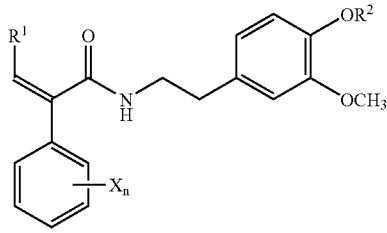

in which the substituents have the following meanings:
- X is hydrogen, halogen, $C_1$–$C_4$-alkyl, $C_1$–$C_4$-haloalkyl, $C_1$–$C_4$-alkoxy or $C_1$–$C_4$-haloalkoxy, in which X is in the 3- or 4-position;
- n is 1 or 2, it being possible for X to be different if n represents 2;
- $R^1$ is n-propyl, isopropyl, tert-butyl, $C_1$–$C_4$-haloalkyl, $C_3$–$C_5$-cycloalkyl, $C_1$–$C_4$-alkoxy, $C_1$–$C_4$-haloalkoxy, aziridinyl or oxiranyl; and
- $R^2$ is hydrogen $C_1$–$C_4$-alkyl, $C_1$–$C_2$-haloalkyl, allyl, propargyl or $CH_2C{\equiv}C$—$C_1$–$C_4$-alkyl.

2. An acrylamide of the formula I as claimed in claim 1, wherein X is a halogen in the 4 position.

3. An acrylamide of the formula I as claimed in claim 1, wherein $R^1$ is isopropyl, tert-butyl, cyclopropyl, trifluoromethyl, methoxy, ethoxy or trifluoromethoxy.

4. A process for the preparation of a compound as claimed in claim 1, which comprises reacting a carboxylic acid of the formula II,

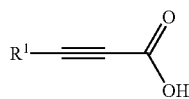

in which $R^1$ has the meanings given for formula I, with a phenethylamine of the formula III,

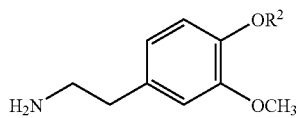

in which $R^2$ has the meanings given for formula I, to give a phenethylamine of the formula IV

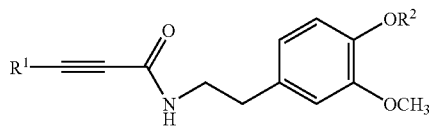

which is converted with trialkyltin hydrode into the organotin compound of the formula V

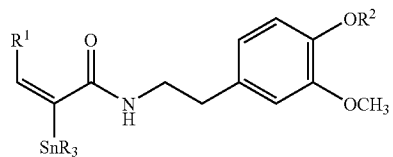

in which R is $C_1$–$C_6$-alkyl, which compound is converted, by transition metal catalysis with phenyl halides of the formula VI

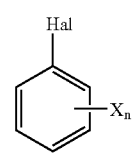

in which Hal is bromine or iodine, into the compounds of the formula I.

5. A composition suitable for the control of harmful phytopathogenic fungi, comprising a solid or liquid carrier and a compound of the formula I as claimed in claim 1.

6. A process for controlling harmful phytopathogenic fungi comprising forming an intermediate of the Z-substituted acrylamide of the formula I of claim 1, wherein $R^2$ represents a hydrogen.

7. A process for controlling harmful phytopathogenic fungi, which comprises treating the fungi or the materials, plants, soil or seeds to be protected from fungal attack with an effective amount of a compound of formula I as claimed in claim 1.

8. An acrylamide of the formula I as claimed in claim 2, wherein $R^1$ is isopropyl, tert-butyl, cyclopropyl, trifluoromethyl, methoxy, ethoxy or trifluoromethoxy.

9. A process for the preparation of a compound as claimed in claim 3, which comprises reacting a carboxylic acid of the formula II,

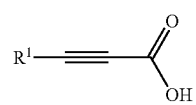

in which $R^1$ has the meanings given for formula 1, with a phenethylamine of the formula III,

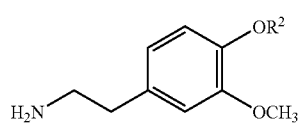

in which R² has the meanings given for formula I, to give a phenethylamide of the formula IV

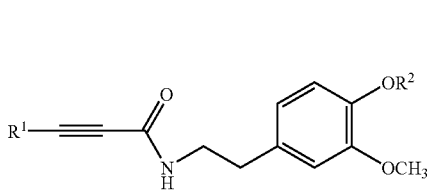

IV which is converted with trialkyltin hydrode into the organotin compound of the formula V

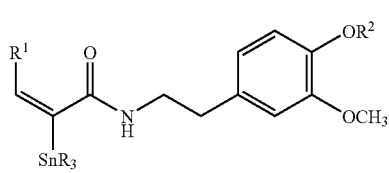

V in which R is $C_1$–$C_6$-alkyl, which compound is converted, by transition metal catalysis with phenyl halides of the formula VI

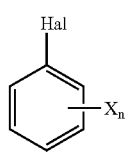

VI in which Hal is bromine or iodine, into the compounds of the formula I.

10. A process for the preparation of a compound as claimed in claim 1, which comprises reacting a carboxylic acid of the formula II,

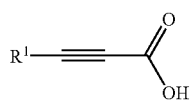

II in which R¹ has the meanings given for formula I, with a phenethylamine of the formula III,

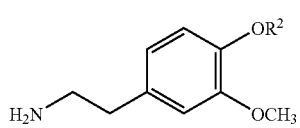

III in which R² has the meanings given for formula I, to give a phenethylamide of the formula IV

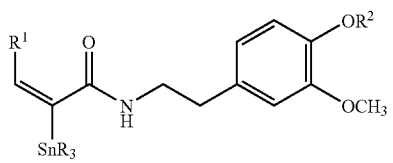

V which is converted with trialkyltin hydrode into the organotin compound of the formula V

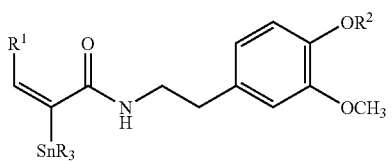

V in which R is $C_1$–$C_6$-alkyl, which compound is converted, by transition metal catalysis with phenyl halides of the formula VI

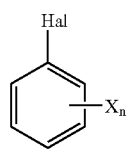

VI in which Hal is bromine or iodine, into the compounds of the formula I.

11. A composition suitable for the control of harmful phytopathogenic fungi, comprising a solid or liquid carrier and a compound of the formula I as claimed in claim 2.

12. A composition suitable for the control of harmful phytopathogenic fungi, comprising a solid or liquid carrier and a compound of the formula I as claimed in claim 3.

13. A process far controlling harmful phytopathogenic fungi comprising forming an intermediate of the Z-substituted acrylamide of the formula I of claim 2, wherein R² represents a hydrogen.

14. A process for controlling harmful phytopathogenic fungi comprising forming an intermediate of the Z-substituted acrylamide of the formula I of claim 3, wherein R² represents a hydrogen.

15. A process for controlling harmful phytopathogenic fungi, witch comprises treating the fungi or the materials, plants, soil or seeds to be protected from fungal attack with an effective amount of a compound of formula I as claimed in claim 2.

16. A process for controlling harmful phytopathogenic fungi, which comprises treating the fungi or the materials, plants, soil or seeds to be protected from fungal attack with an effective amount of a compound of formula I as claimed in claim 3.

17. An acrylamide of the formula I as claimed in claim 1, wherein $R^1$ is tert-butyl, $C_1$–$C_4$-haloalkyl, $C_3$–$C_5$-cycloalkyl, $C_1$–$C_4$-alkoxy, $C_1$–$C_4$-haloalkoxy, aziridinyl or oxiranyl.

18. An acrylamide of the formula I as claimed in claim 1, wherein $R^1$ is isopropyl, tert-butyl, $C_1$–$C_4$-haloalkyl, $C_3$–$C_5$-cycloalkyl, $C_1$–$C_4$-alkoxy, $C_1$–$C_4$-haloalkoxy, aziridinyl or oxiranyl.

19. An acrylamide of the formula I as claimed in claim 2, wherein $R^1$ is tert-butyl, cyclopropyl, trifluoromethyl, methoxy, ethoxy or trifluoromethoxy.

* * * * *